US007075715B2

(12) United States Patent
Muller et al.

(10) Patent No.: US 7,075,715 B2
(45) Date of Patent: Jul. 11, 2006

(54) MOUTH SWITCH ARRANGEMENT AND MICROSCOPE WITH MOUTH SWITCH ARRANGEMENT

(75) Inventors: Roland Muller, Aalen (DE); Joseph Schlosser, Aalen-Ebnat (DE)

(73) Assignee: Carl Zeiss Stiftung, Heidenheim (DE)

( * ) Notice: Subject to any disclaimer, the term of this patent is extended or adjusted under 35 U.S.C. 154(b) by 58 days.

(21) Appl. No.: 10/619,447

(22) Filed: Jul. 16, 2003

(65) Prior Publication Data

US 2004/0090668 A1   May 13, 2004

(30) Foreign Application Priority Data

Jul. 18, 2002   (DE) .............................. 102 32 688

(51) Int. Cl.
*G02B 21/00* (2006.01)

(52) U.S. Cl. ...................... 359/368; 359/375; 359/503

(58) Field of Classification Search ........ 359/368–384, 359/894
See application file for complete search history.

(56) References Cited

U.S. PATENT DOCUMENTS 3,762,797 A * 10/1973 Heller ........................ 359/375
3,877,778 A * 4/1975 Heller ........................ 359/503
3,887,267 A    6/1975 Heller ........................ 359/368

FOREIGN PATENT DOCUMENTS

| CA | 957355 | 11/1974 |
| CH | 526 069 | 7/1972 |
| DE | 24 18 565 C3 | 1/1975 |

OTHER PUBLICATIONS

Carl Zeiss Brochure, "OPMI Neuro/NC4 System—The Standard of Excellence", Germany (2001).

* cited by examiner

*Primary Examiner*—Thong Q Nguyen
(74) *Attorney, Agent, or Firm*—Potomac Patent Group PLLC (57) ABSTRACT

A mouth switch arrangement comprises a mouth switch operable by a mouth of an operator and attachable by a holding device to a base part. The holding device comprises a mouth switch support having a locking member shiftable in a longitudinal direction of a rod of the holding device and a pivot member pivotable about the locking member. The mouth switch is provided for use on a surgical stereo microscope.

15 Claims, 8 Drawing Sheets

MOUTH SWITCH ARRANGEMENT AND MICROSCOPE WITH MOUTH SWITCH ARRANGEMENT

FIELD OF THE INVENTION

The invention relates to a mouth switch arrangement to be mounted on an instrument and to be operated with the mouth of an operator of the instrument. A mouth switch serves to start operations, which are otherwise possibly started with a hand switch, hand key button or foot switch, with the mouth. The use of a mouth switch is particularly advantageous in cases when the operator has no free hand to manually perform the desired operation of a switch.

In particular, the mouth switch arrangement is provided for use on an optical instrument, such as a microscope and, in particular, a surgical microscope.

BACKGROUND OF THE INVENTION

U.S. Pat. No. 3,887,267 discloses a surgical microscope having a mouth switch arrangement comprising a mouth switch for operation with the operators mouth and a rod for mounting the mouth switch on the surgical microscope. On the rod there is mounted a mouth switch support so as to be longitudinally shiftable and lockable by means of an adjusting screw. Due to the mouth switch being longitudinally shiftable on the rod, it is possible to adjust the mouth switch relative to oculars of the microscope, so that the operator can look into the microscope and, at the same time, can operate the mouth switch with the mouth. In situations in which the arrangement of the mouth swicth near the oculars is irritating for the operator, the adjusting screw can be unlocked and the mouth switch can be pivoted away around the rod or can be shifted therealong.

Unlocking of the adjusting screw for removing the mouth switch from its operation position is felt to be complicated and inconvenient in practice. In particular, after such unlocking, it is complicated to reposition the mouth switch precisely in the desired operation position again, in which it is operable by the operator in the desired head position, i.e., during observation through the microscope.

SUMMARY OF THE INVENTION

The present invention was made in view of the aforementioned problems, and it is an object of the present invention to propose a mouth switch arrangement which facilitates a temporary removal of a mouth switch from its operation position and a subsequent return of the mouth switch into its operation position.

For this purpose, the invention proceeds out from a mouth switch arrangement having a mouth switch to be operated with a mouth of an operator and a holding device for the mouth switch for displaceably mounting the mouth switch on a base part, the holding device comprising a rod and a mouth switch support fixed to the rod so as to be longitudinally shiftable.

According to an embodiment the mouth switch support comprises a locking member which is shiftable on the rod and a pivot member which is pivotable relative to the locking member and which supports the mouth switch.

The invention is based on the concept of allocating the function of positioning the mouth switch in the longitudinal rod direction and the function of removing and returning the mouth switch from and back to its operation position, respectively, to different components of the mouth switch support. Accordingly, the function of adjusting the mouth switch along the rod is allocated to the locking member and it is the pivot member, which supports the mouth switch and which is pivotable relative to the locking member, which is provided to remove the mouth switch with ease from its operation position by pivoting the same and subsequently, reposition it in its operation position by pivoting back.

Preferably, a latch mechanism is provided between the locking member and the pivot member to prevent, in a latched state, the pivot member from pivoting relative to the locking member, so that the mouth switch is fixedly disposed in its operation position and to allow, in its unlatched state, a pivoting of the two components relative to each other.

Here, the latch mechanism is preferably biased in its latched state, so that by operating a handle, for example against a spring force, the latch mechanism is adapted to be transferred into its unlatched state. This allows, when the mouth switch is returned from its pivoted-away position to its operation position, the latch mechanism to be automatically latched in the operation position, so that no separate adjusting steps are necessary in this case.

The pivot member is pivoted relative to the locking member, preferably about the rod. Accordingly, the pivot member preferably comprises a sleeve engaging at least partly around the rod.

A preferred application of the mouth switch arrangement resides in the mounting of the same on a microscope.

The microscope comprises a microscopy optics having several lenses accommodated in a chassis of the microscope. Here, the chassis further also forms the base part for directly or indirectly mounting the rod of the mouth switch arrangement thereon.

In a microscope which includes a main chassis for accommodating an objective and a tube removable therefrom as a chassis for accommodating an ocular, the main body and the tube, preferably, are each provided with a joining flange for joining the two components with each other. In this case, the rod is preferably mounted on one of the two flanges.

In this case, the holding device of the mouth switch arrangement preferably comprises a latch ring fixedly connected to the rod and adapted to be brought in latching engagement with the flange, and this preferably in cases when the tube is removed from the main body.

With the mouth switch the operator can operate a plurality of microscope functions such as turning on and off an extra illumination or the like. Preferably, however, the mouth switch is used for cancelling a locking of movements of a microscope stand.

Preferred embodiments of the invention will hereinafter be described in more detail with reference to the accompanying drawings.

DETAILED DESCRIPTION

Figure 1:
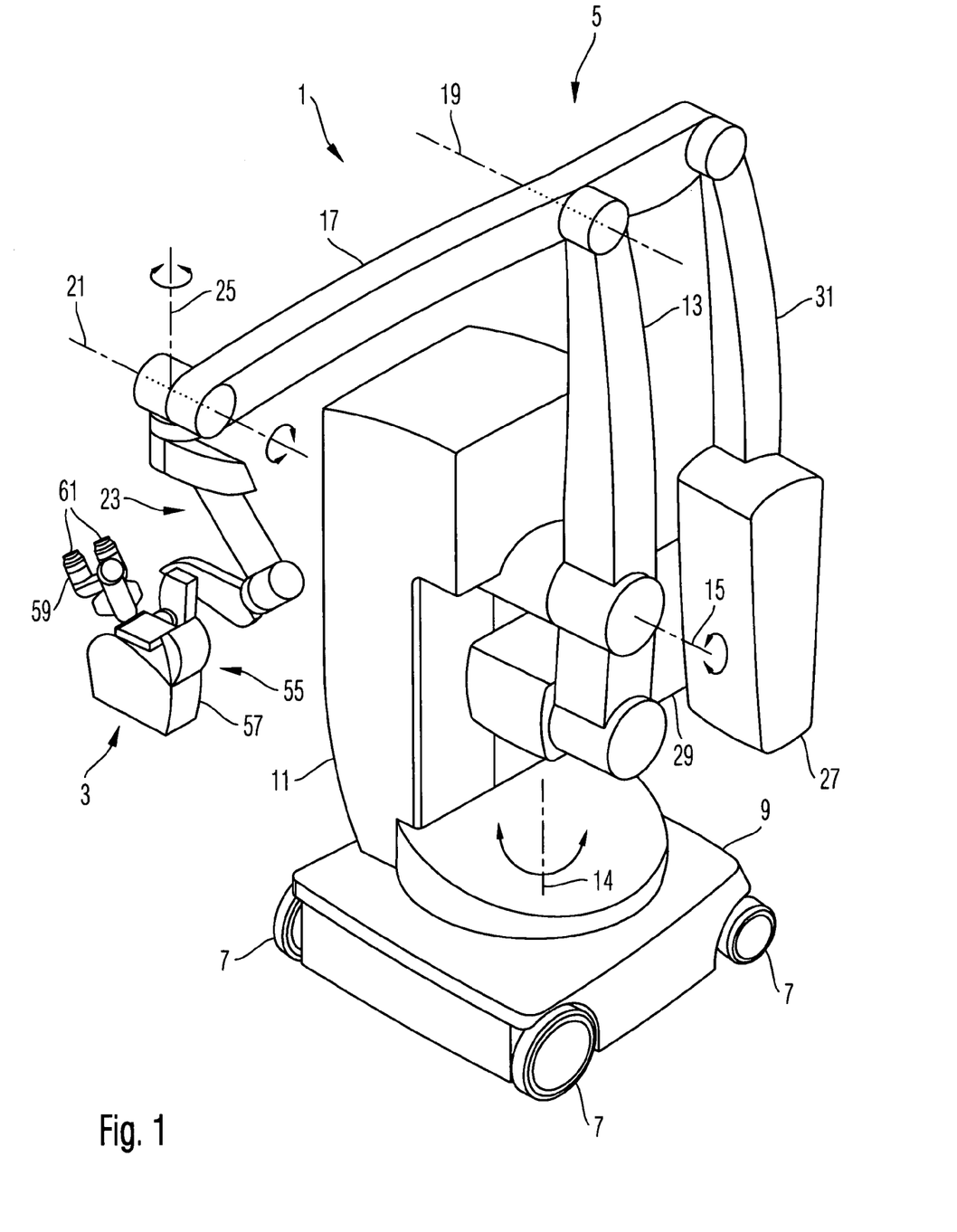
FIG. 1 is a perspective representation of a stereomicroscope arrangement with stand.

A microscopy arrangement 1 perspectively represented in FIG. 1 comprises a surgical stereomicroscope 3 mounted on a stand 5. The stand 5 comprises a stand foot 9 provided with wheels 7 on which a base part 11 is mounted so as to be rotated about a vertical axis 14. Mounted on the base part 11, is a stand arm 13 adapted to be pivoted about a horizontal axis 15 and, at an upper end of the arm 13, there is provided a further arm 17 adapted to be pivoted about a further horizontal axis 19. At a front end of the arm 17, the microscope 3 is suspended pivotably about a further horizontal axis 21 through intermediate members 23, which allow a rotation of the microscope 3 about a further vertical axis 25 and about further axes, not shown in FIG. 1, for adjusting a viewing direction of the microscope.

The stand 5 allows the microscope 3 to be balanced such that it is displaceable in space by exerting comparatively small forces. For this purpose, the stand 5 comprises a counterbalance 27 which is coupled to the arms 13 and 17 through additional arms 29 and 31.

Figure 3:
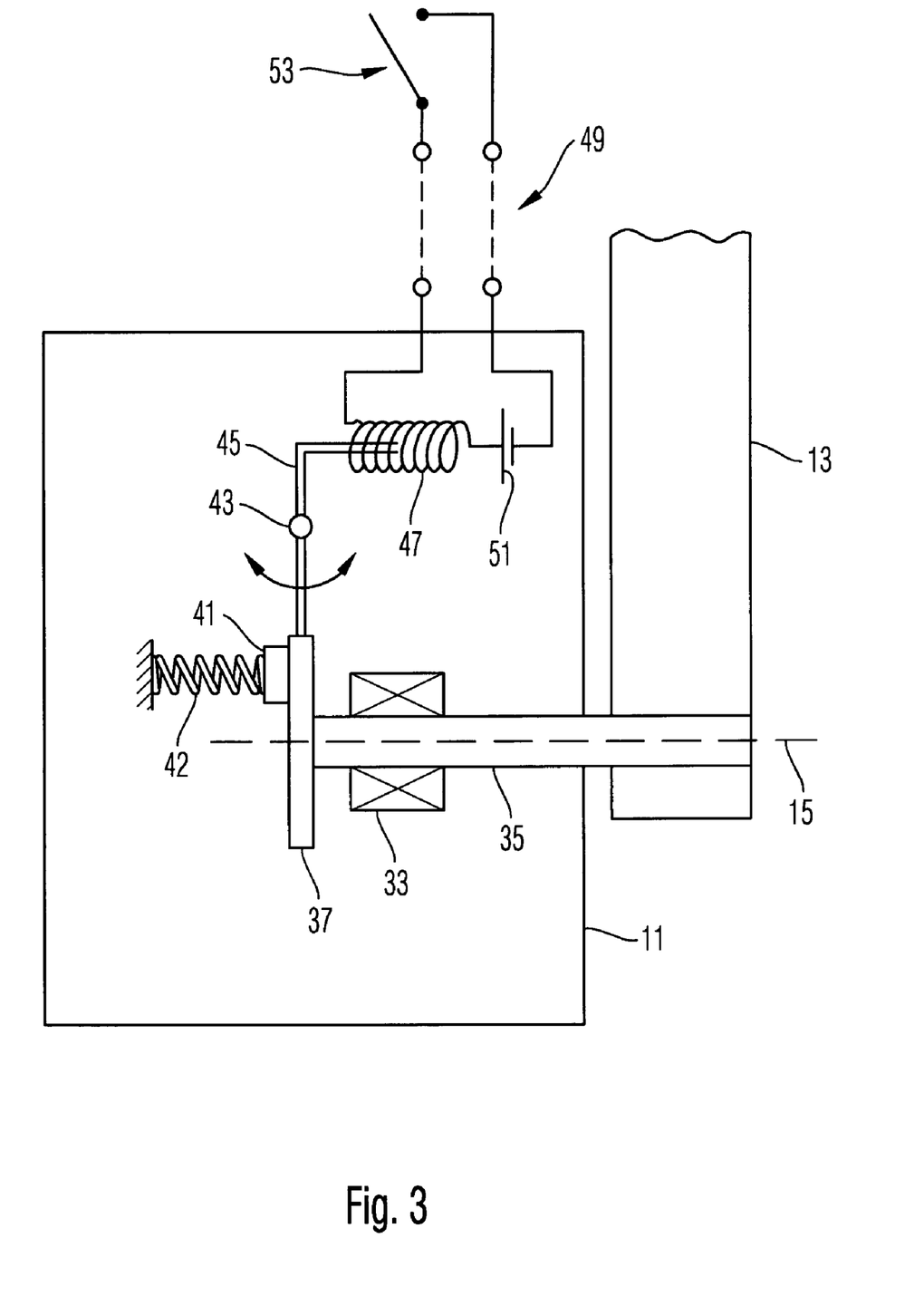
FIG. 3 is a schematic representation of a blocking of components of the stand of the microscope shown in FIG. 1.

To prevent the microscope 3 from being displaced in space unintentionally, individual pivot axes, such as axis 15, are locked against rotation of its components as is schematically illustrated with reference to FIG. 3. In the base part 11, there is provided a bearing 33 for a shaft 35 which supports the arm 13. A brake disc 37 is fixedly mounted on one end of the shaft 35 for rotation therewith, against which a brake pad 41 is pressed by means of a pressure spring 42, the brake pad being fixedly connected with the base part 11 for rotation therewith. Hence, the brake pad 41 pressed against the disc 37 prevents the arm 13 from being pivoted relative to the base part 11. The brake pad 41 is connected with a lever 45, which is pivotable about an axis 43, such that the brake pad 41 can be lifted out of contact with the disc 37 by pivoting the lever 45 about the axis 43. Such a disengagement of the brake pad 41 from the disc 37 is achieved by exciting a magnetic winding 47. To this end, an electric circuit 49 is closed which comprises a current source 51 and a switch 53 positioned remote from the base part 11 and opened in its inoperative position. Consequently, by operating the switch 53, the current flow is opened through the winding 47, the latter draws the lever 45 to a position such that the brake pad 41 is lifted from the disc 37 and then, the arm 13 is freely pivotable about the axis 15 relative to the base part 11.

The microscope 3 has a multipart chassis 55 including a main body 57 (see FIG. 1) which, among others, accommodates an objective of the microscopy optics and is coupled to the stand 5. A tube 59 is coupled with the main body 57 to form a chassis for the oculars 61 of the microscope 3.

Figure 2:
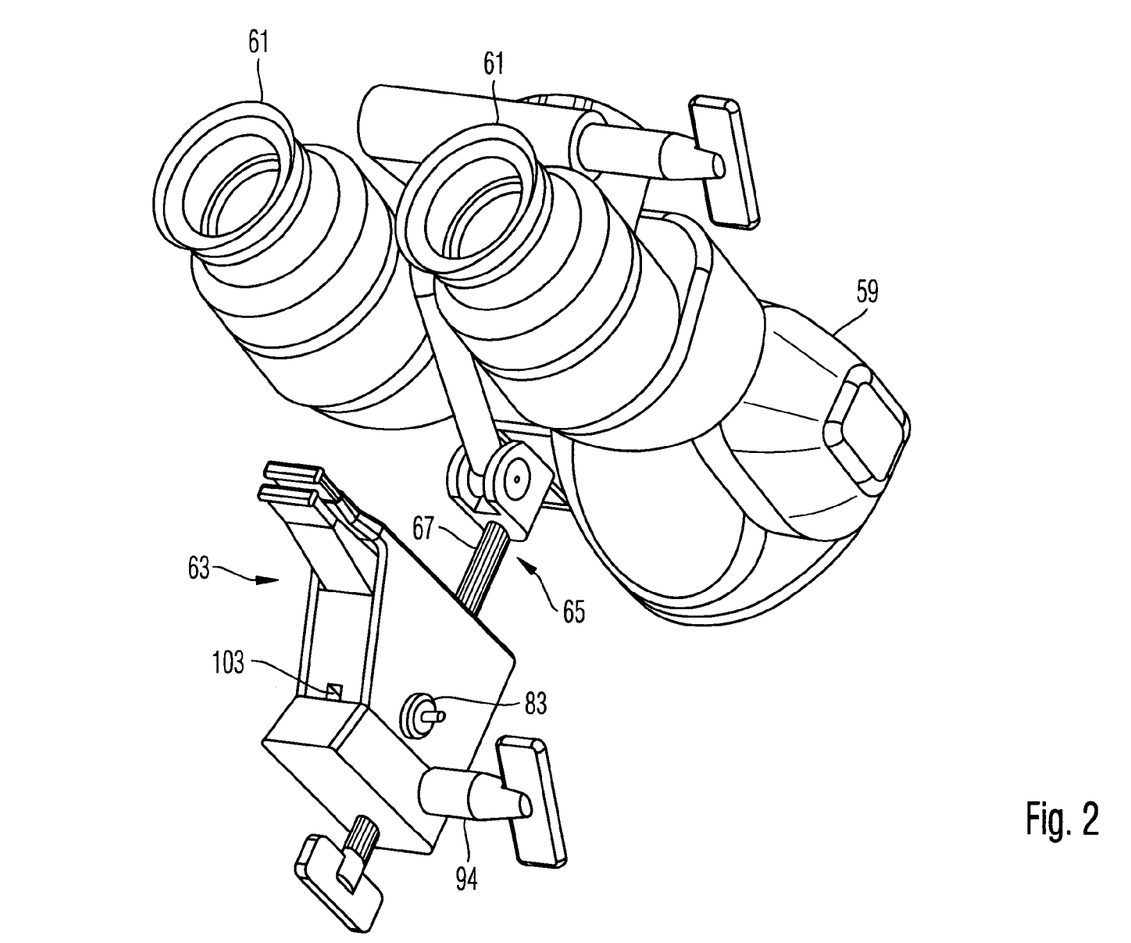
FIG. 2 is a perspective representation of a tube of the microscope of FIG. 1 on which a mouth switch is mounted.

FIG. 2 perspectively shows the tube 59 including the oculars 61. Furthermore, it is evident from FIG. 2, that a mouth switch 63 is mounted on the tube 59 through a holding device 65. The holding device 65 comprises a rod 67 to which the mouth switch 63 is attached so as to be longitudinally shiftable.

Figure 4:
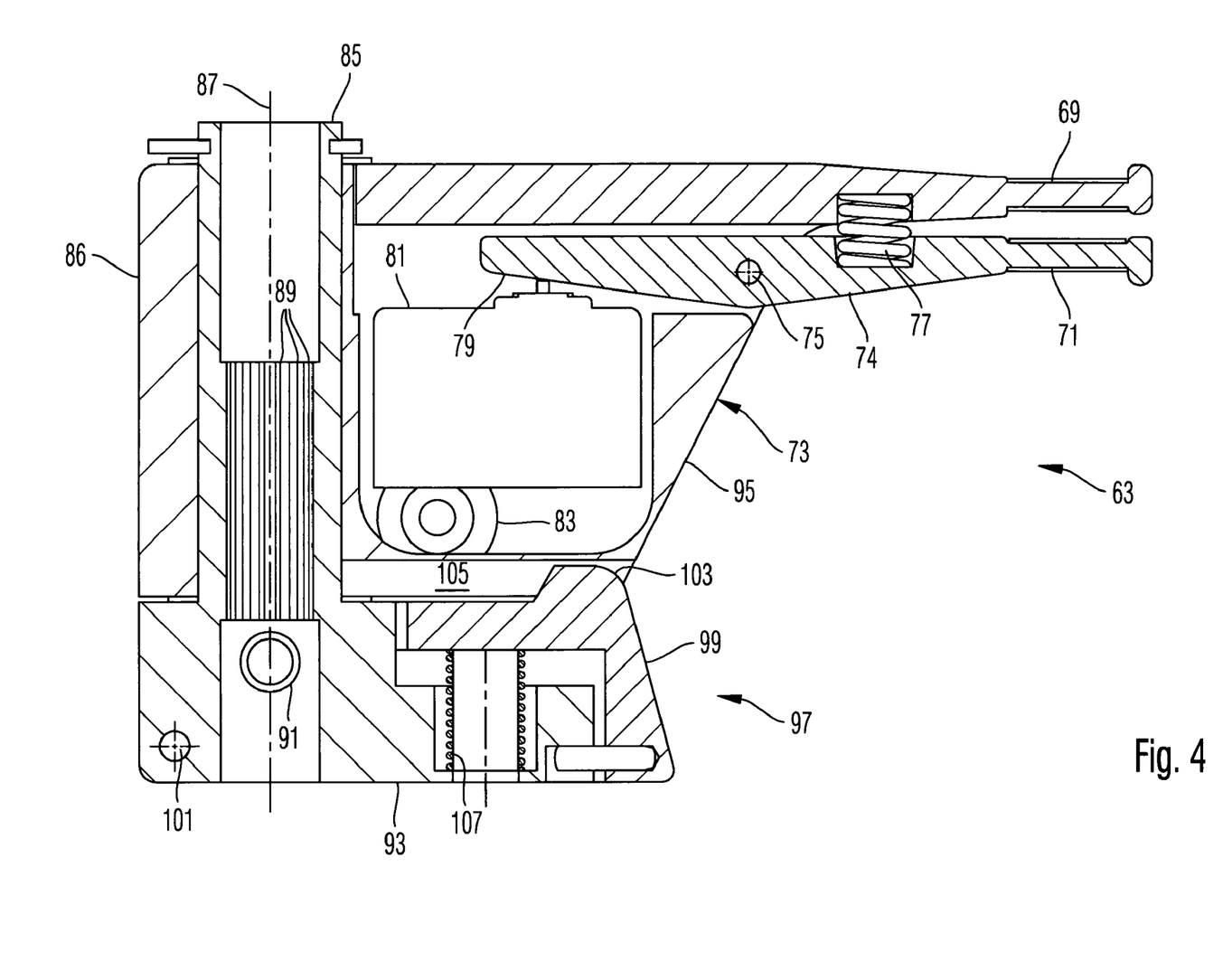
FIG. 4 is a sectional view of the mouth switch of FIG. 2 in its latched state.
Figure 5:
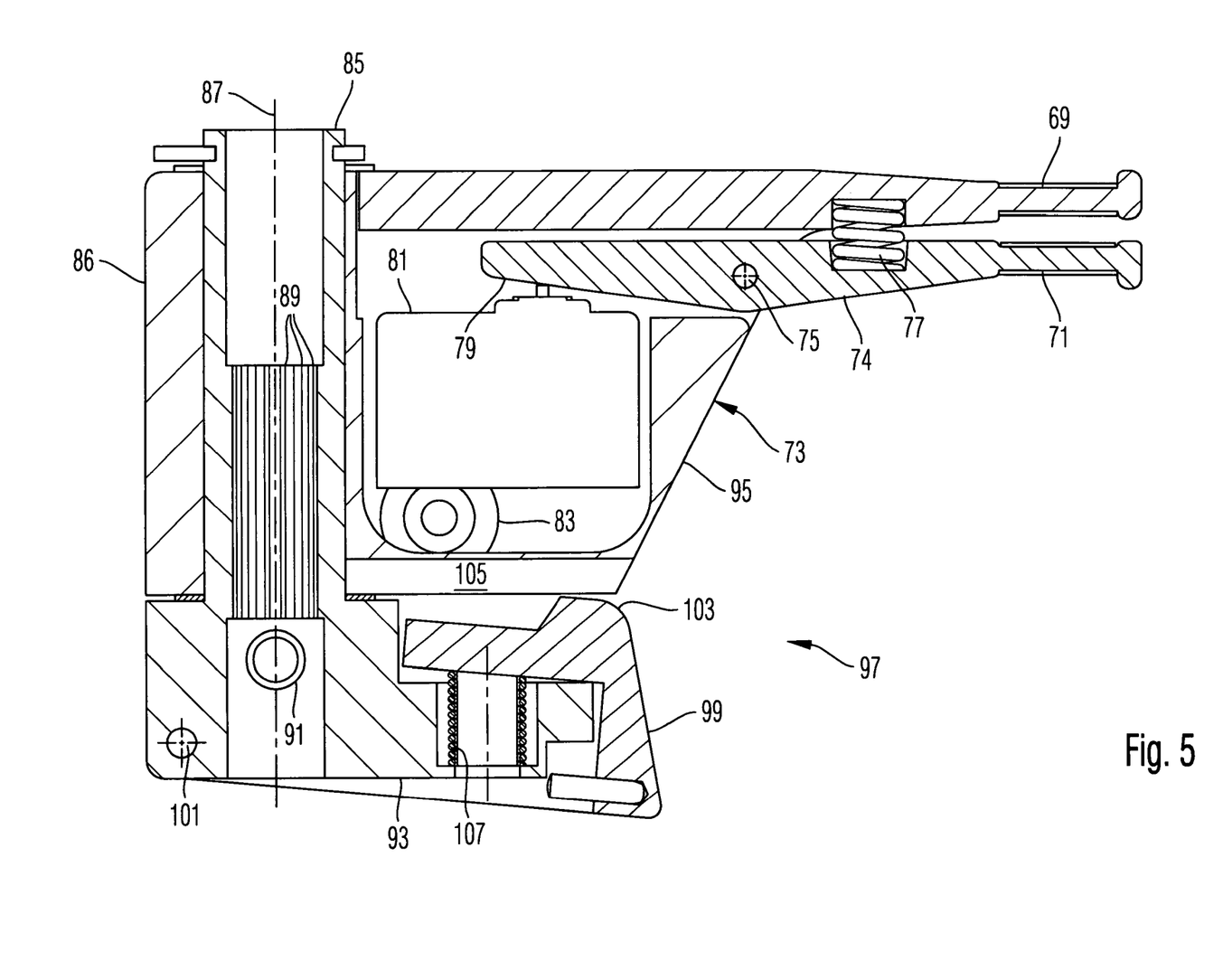
FIG. 5 is a representation of the mouth switch corresponding to FIG. 4, but in its unlatched state.

FIGS. 4 and 5 represent a sectional view of the mouth switch 63. The latter comprises an upper mouthpiece 69 and a lower mouthpiece 71 which are spaced apart from each other and both of which can be received by the operators mouth. The upper mouthpiece 69 is fixedly mounted on a pivot member 95 of the mouth switch 63, while the lower mouthpiece 71 is pivotable on a mouthpiece lever 74 about an axis 75 relative to a mouth switch support 73. A spring 77 is biased between the two mouthpieces 69, 71 to keep the latter at a distance from each other. The operators lips or teeth can exert a force on the mouthpieces 69, 71, so that the latter pivot about the axis 75 towards one another against the force of the spring 77. In doing so, an end 79 of the mouthpiece lever 74 opposite to the lower mouthpiece 71 presses against a contact switch 81 to close an electric contact, not shown in FIG. 4.

In addition, a change-over switch 83 is provided outside on the mouth switch 63 to be operated by the operators hand to close a further electric contact. The electric contacts of the contact switch 81 and the change-over switch 83 are connected in series and together form the switch 53 of FIG. 3 to release the brakes of the stand 5. Hence, through the change-over switch 83, the function of the mouth switch can be activated and deactivated, respectively. Upon activation, the operator then can release the brakes of the stand 5 by pressing the two mouthpieces 69, 71 together and he can also exert force on the microscope 3 via the mouthpieces 69, 71 to displace the latter in space on the stand 5.

A locking member 93 of the mouth switch support 73 comprises a sleeve 85 which is provided in an inner area with profile ribs 89 extending in parallel to an axis 87 and which includes a screw hole 91 extending transversely to the axis 87. The inner profile ribs 89 of the sleeve 85 engage profile ribs which are provided outside on the rod 67 of the holding device 65 to lock a rotation of the sleeve 85 about the central axis 87 of the rod 67. A locking screw 94 is screwed into the screw hole 91, which screw, when being tightly screwed down, prevents the sleeve 85 from being shifted in the longitudinal direction of the rod 67, so that, as a result, the locking member 93 is subsequently locked on the rod 67. By unscrewing the screw 94, the locking member 93 is shiftable in the longitudinal direction of the rod 67.

The mouth switch support 73 further comprises a pivot member 95 having a sleeve 86 engaging the sleeve 85 of the locking member 93, such that the pivot member 95 is pivotable about the axis 87.

A latch mechanism 97 comprises a handle 99 which is pivotable about an axis 101 extending transversely to the axis 87 and which has a rib 103 to engage a groove 105 of the pivot member 95 in the latched position of the latch mechanism 97 as shown in FIG. 4. The rib 103 engaging the groove 105 of the pivot member 95 prevents the pivot member 95 from being pivoted with respect to the locking member 93, so that, in the operation position of the mouth switch 63 shown in FIG. 2, the mouthpieces 69, 71 of the mouth switch 63 mounted on the pivot member 95 are fixedly mounted on the rod 67 for rotation therewith.

The operator can pivot the handle 99 with the hand against the force of a spring 107 about the axis 101 to bring the rib 103 out of engagement with the groove 105 as is shown in FIG. 5. In this unlatched state of the latch mechanism 97, the pivot member 95 of the mouth switch support 73 is pivotable relative to the locking member 93 of the mouth switch support 73, so that the mouthpieces 69, 71 can be pivoted about the rod 67 to remove same from the operation position near the oculars 61 (see FIG. 2).

Figure 6:
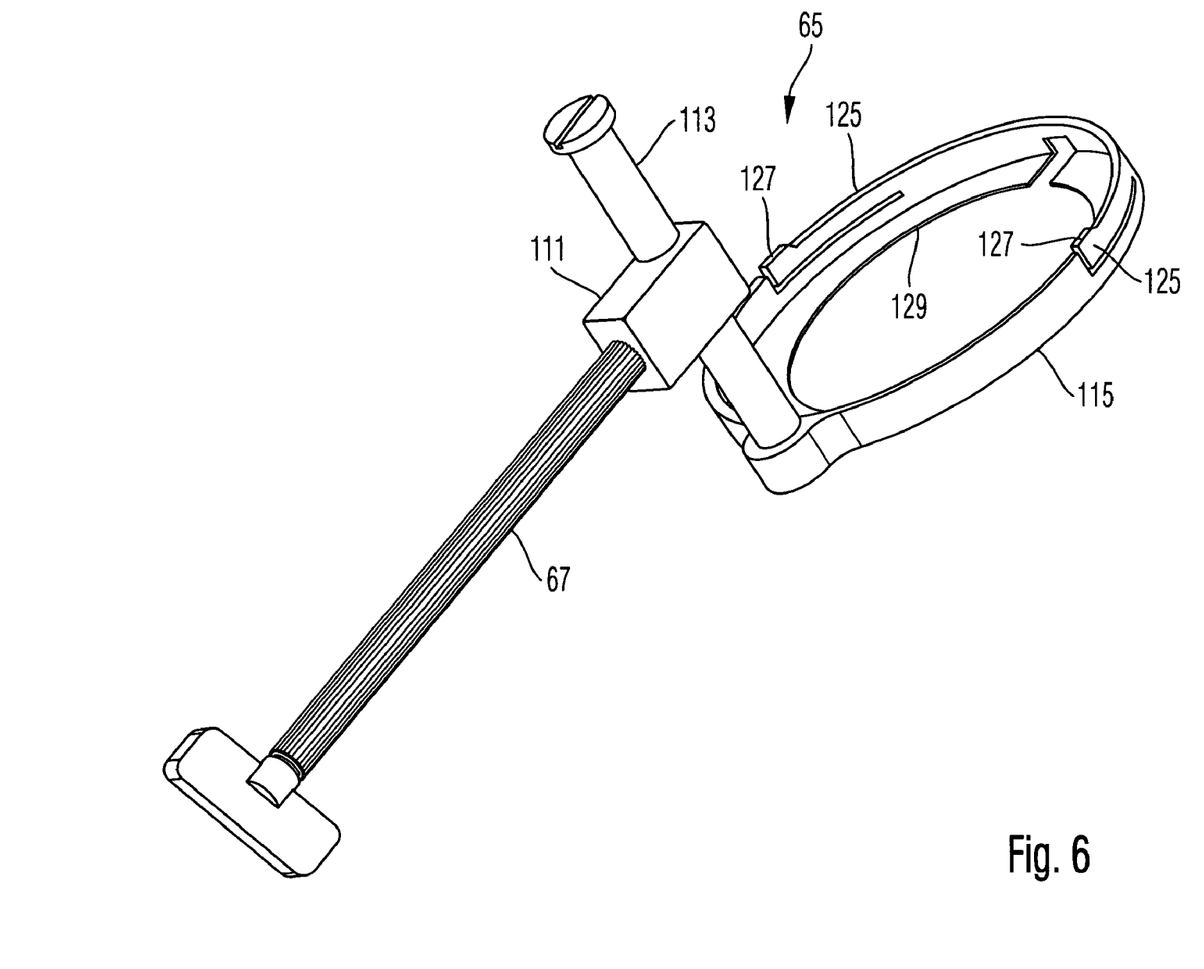
FIG. 6 is a perspective representation of a detail of the holding device of the mouth switch of FIGS. 2, 4 and 5.
Figure 7:
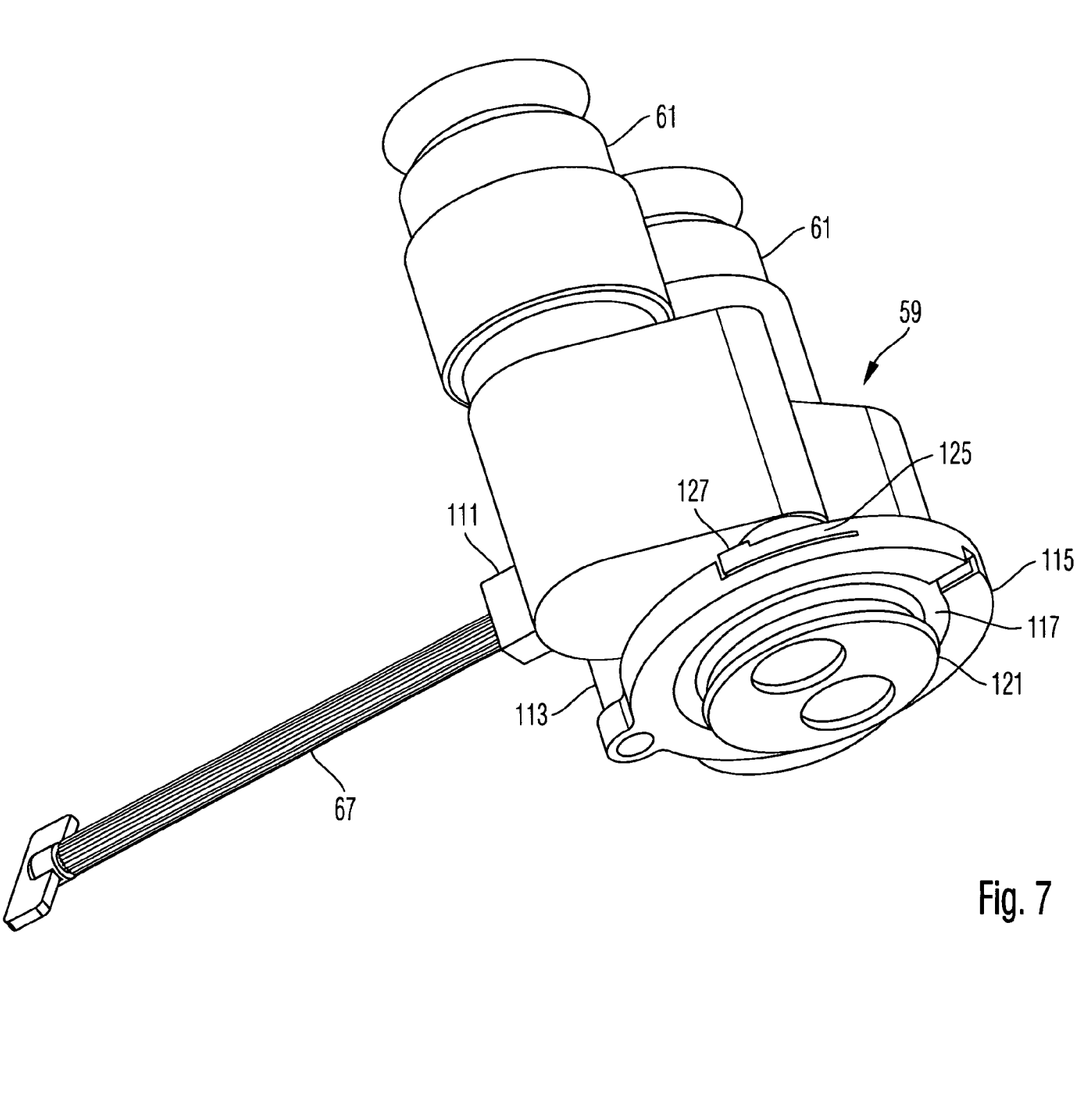
FIG. 7 is a perspective representation of the tube of the microscope of FIG. 1 having mounted thereon a holding device for the mouth switch.
Figure 8:
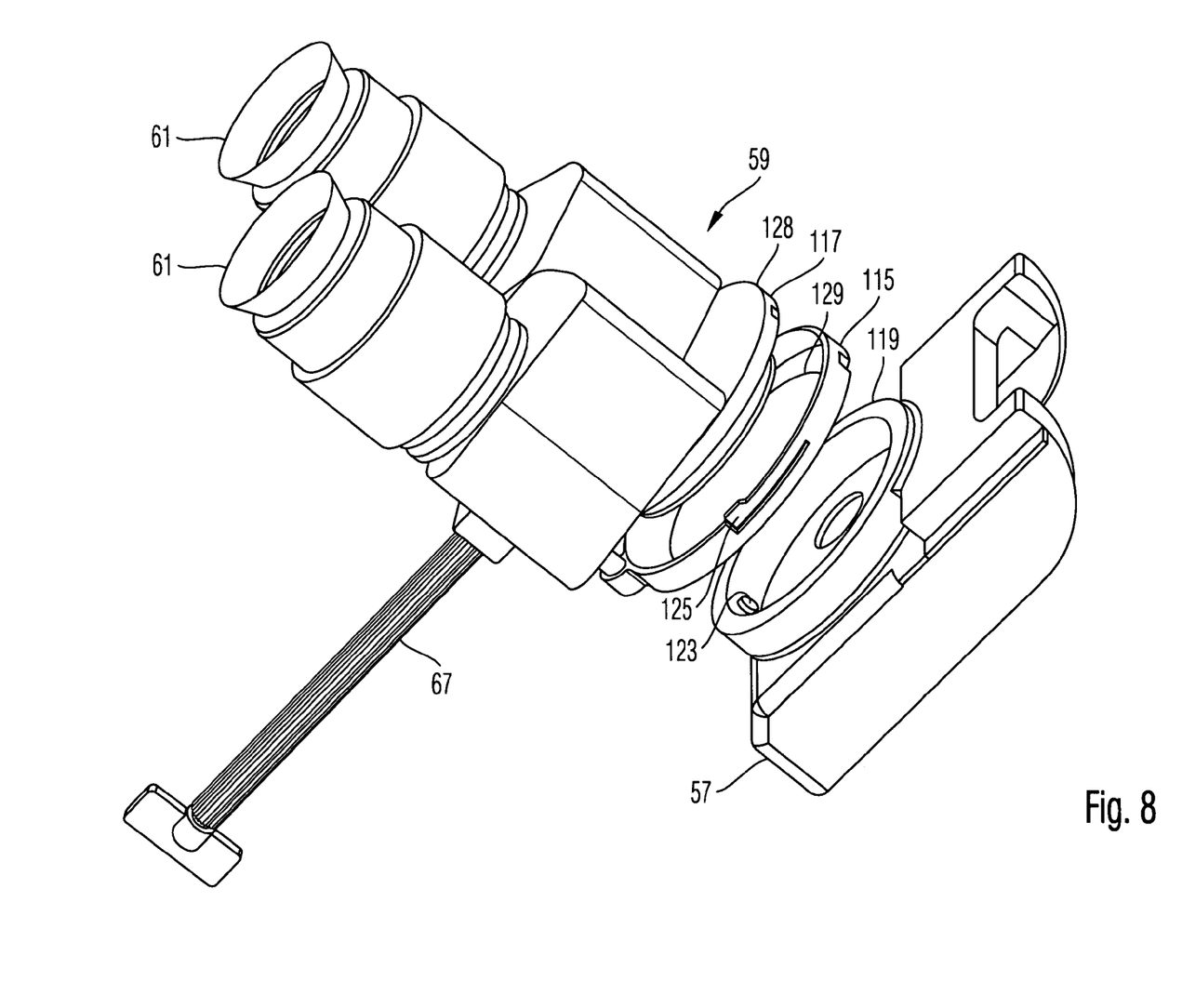
FIG. 8 is a further perspective representation of the tube, the holding device and a part of a main body of the microscope of FIG. 1.

FIGS. 6, 7 and 8 show details of the holding device 65 of the mouth switch 63 and their mounting on the chassis of the microscope 3 between its main body 57 and tube 59.

The rod 67 is connected via a shift piece 111 with a further rod 113 which extends transversely to the rod 67 and is shiftable along the rod 113. The rod 113 is fixedly connected with a latch ring 115. Hence, the shift piece 111 forms the base part of the mouth switch arrangement, so that the shift piece and the base part, respectively, are adapted to be positioned relative to the main body of the microscope. However, it is also possible to make use, for example, of the main body of the microscope or of another component of the microscope or its stand directly as a base part of the mouth switch arrangement. Within the scope of the present invention, the term base part is also intended to comprise a structural group holding the mouth switch arrangement which likewise may be composed of several structural members, which may themselves be displaceable, particularly, relative to each other.

As can be seen from FIG. 8, the tube 59 comprises a joining flange 117 to be coupled with a corresponding joining flange 119 of the main body 57. To this end, the flange 117 comprises a conical projection 121 which, when the flanges 117, 119 are coupled, is inserted into the flange 119. The flange 119 comprises a screw hole 123 for introducing a screw not shown in the Figures which, when the flanges 117, 119 are coupled, is close to the conical projection 121 on the outside to hold the flanges 117 and 119 together.

The latch ring 115 for holding the mouth switch 63 is interposed between the joined flanges 117, 119 and, before the tube 59 is placed on the main body 57, it is latched on the flange 117 of the tube 59, as is shown in FIG. 7. For this purpose, the latch ring comprises two spring blades 125 which extend around the ring 115 in circumferential direction, each of which being provided with a latch nose 127. When the latch ring 115 is placed on the flange 117, the latch noses engage over an edge 128 of the flange 117 of the tube 59 to hold the latch ring 115 and thus the mouth switch 63 during the assembly of the tube 59 on the main body 57. Furthermore, the latch ring 115 includes a ring disc section 129 which is to be arranged between the face areas of the two flanges 117 and 119 disposed towards each other, when the tube 59 is assembled on the main body, so that the mouth switch 63 is then fixedly attached to the microscope 3 by means of the flanges 117 and 119 pressed on each other.

In the foregoing examples, the mouth switch serves to cancel a pivot locking of the microscope stand. As an alternative, it is possible to also use the mouth switch for other purposes, such as turning on and off an extra illumination, altering an operating mode of the microscope such as an operating mode of a data presentation or the like fed into the beam path of the microscope.

Furthermore, it is also possible to provide the mouth switch on devices other than microscopes. Its holding allows the mouth switch to be pivoted with ease out of the working area of the operator and to be subsequently pivoted with ease back into this working area.

The invention claimed is:

1. A mouth switch arrangement, comprising:
a mouth switch operable with a mouth of an operator, and
a mouth switch mount for displaceably mounting the mouth switch on a first base, the mouth switch mount comprising:
a rod; and
a support fixed to the rod and shiftable in a longitudinal direction of the rod, wherein the support comprises:
a locking member shiftable on the rod in the longitudinal direction; and
a pivot member pivotable relative to the locking member and supporting the mouth switch.

2. The mouth switch arrangement of claim 1, wherein the locking member and the pivot member are coupled with each other by a latch mechanism, said latch mechanism blocking pivoting of the pivoting member relative to the locking member when the mechanism is in a latched state and allowing the pivoting when the mechanism is in an unlatched state.

3. The mouth switch arrangement of claim 2, wherein the latch mechanism comprises a handle mounted on the locking member for bringing the latch mechanism from a latched state to an unlatched state.

4. The mouth switch arrangement of claim 3, wherein the latch mechanism comprises a spring for biasing the handle in position to hold the latch mechanism in the latched state.

5. The mouth switch arrangement of claim 1, wherein the pivot member is pivotable about a pivot axis extending parallel to the longitudinal direction of the rod.

6. The mouth switch arrangement of claim 1, wherein the pivot member comprises a sleeve extending at least partly around the rod.

7. The mouth switch arrangement of claim 6, wherein the locking member comprises a sleeve extending at least partly around the rod and the sleeve of the pivot member extends at least partly around the sleeve of the locking member.

8. The mouth switch arrangement of claim 1, wherein the first base is displaceable relative to a joining part in order to adjustably position the first base relative to a second base.

9. A microscopy arrangement comprising:
a microscopy optics having plural lenses,
a chassis for accommodating the microscopy optics,
a mouth switch arrangement including:
a mouth switch operable with a mouth of an operator, and
a mouth switch mount for displaceably mounting the mouth switch on a first base, the mouth switch mount comprising:
a rod attached to the chassis; and
a support fixed to the rod and shiftable in a longitudinal direction of the rod wherein the support comprises:
a locking member shiftable on the rod in the longitudinal direction; and
a pivot member pivotable relative to the locking member and supporting the mouth switch.

10. The microscopy arrangement of claim 9, wherein the microscopy optics comprises an objective lens; and at least one ocular wherein further the chassis comprises a main body for accommodating the objective lens and a tube for accommodating the ocular, the main body and the tube each comprising a joining flange for joining the main body and the tube with each other and the rod is attached to one of the flanges.

11. The microscopy arrangement of claim 10, wherein the mouth switch mount comprises a snap ring fixedly connected to the rod and adapted to be brought in a snap engagement with one of the flanges.

12. The microscopy arrangement of claim 9, further comprising a stand for holding the chassis, the stand comprising at least one pivot arm, wherein a brake is provided to block a pivotal movement of the pivot arm on the stand and wherein the mouth switch is configured to operate the brake.

13. The microscopy arrangement of claim 9, wherein the locking member and the pivot member are coupled with each other by a latch mechanism, said latch mechanism blocking pivoting of the pivoting member relative to the locking member when the mechanism is in a latched state and allowing the pivoting when the mechanism is in an unlatched state.

14. The microscopy arrangement of claim 13, wherein the latch mechanism comprises a handle mounted on the locking member for shifting the latch mechanism from the latched state to the unlatched state.

15. The mouth switch arrangement of claim 9, wherein the pivot member is pivotable about a pivot axis extending parallel to the longitudinal direction of the rod.

* * * * *